US010613173B2

(12) United States Patent
Kannengiesser et al.

(10) Patent No.: US 10,613,173 B2
(45) Date of Patent: Apr. 7, 2020

(54) METHOD AND MAGNETIC RESONANCE APPARATUS FOR GENERATING A FAT FRACTION-CORRECTED T1 PARAMETER MAP

(71) Applicants: Siemens Healthcare GmbH, Erlangen (DE); Duke University, Durham, NC (US)

(72) Inventors: Stephan Kannengiesser, Wuppertal (DE); Berthold Kiefer, Erlangen (DE); Mustafa R. Bashir, Cary, NC (US); Claudia Fellner, Lappersdorf (DE); Marcel Dominik Nickel, Herzogenaurach (DE)

(73) Assignees: Siemens Healthcare GmbH, Erlangen (DE); Duke University, Durham, NC (US)

( * ) Notice: Subject to any disclaimer, the term of this patent is extended or adjusted under 35 U.S.C. 154(b) by 43 days.

(21) Appl. No.: 15/946,802

(22) Filed: Apr. 6, 2018

(65) Prior Publication Data
US 2018/0292485 A1 Oct. 11, 2018

Related U.S. Application Data

(60) Provisional application No. 62/482,929, filed on Apr. 7, 2017.

(51) Int. Cl.
*G01R 33/48* (2006.01)
*G01R 33/56* (2006.01)
(Continued)

(52) U.S. Cl.
CPC .......... *G01R 33/4828* (2013.01); *A61B 5/055* (2013.01); *A61B 5/4244* (2013.01);
(Continued)

(58) Field of Classification Search
CPC ............... G01R 33/4828; G01R 33/50; G01R 33/5602; G01R 33/5613; G01R 33/5608;
(Continued)

(56) References Cited

U.S. PATENT DOCUMENTS

| 10,162,031 B2 | 12/2018 | Tunnicliffee et al. |
| 2011/0096974 A1* | 4/2011 | Gilson ............... G01R 33/4828 382/131 |
| 2015/0042334 A1 | 2/2015 | Kannengiesser et al. |

FOREIGN PATENT DOCUMENTS

WO 2014140635 A1 9/2014

OTHER PUBLICATIONS

Hoad CL et al.,Palaniyappan N, Kaye P et al. A study of T1 relaxation time as a measure of liver fibrosis and the influence of confounding histological factors. NMR Biomed. 2015; 28(6):706-714.
(Continued)

*Primary Examiner* — Susan S Lee
(74) *Attorney, Agent, or Firm* — Schiff Hardin LLP

(57) ABSTRACT

In a magnetic resonance (MR) apparatus and a method for operating such an apparatus, a T1 parameter map is generated with fat fraction correction, by using a model in which the fat fraction of acquired MR data is used as a known parameter. The T1 values from the acquired MR data are fat fraction-corrected in such a manner, so as to generate fat fraction-corrected entries for the T1 parameter map according to the model.

14 Claims, 1 Drawing Sheet

(51) Int. Cl.
 G01R 33/565 (2006.01)
 A61B 5/055 (2006.01)
 G01R 33/50 (2006.01)
 A61B 5/00 (2006.01)
 G01R 33/561 (2006.01)
(52) U.S. Cl.
 CPC ............ *A61B 5/4872* (2013.01); *G01R 33/50* (2013.01); *G01R 33/5602* (2013.01); *G01R 33/565* (2013.01); *G01R 33/5608* (2013.01); *G01R 33/5613* (2013.01)
(58) Field of Classification Search
 CPC ... G01R 33/565; A61B 5/4872; A61B 5/4244; A61B 5/055
 See application file for complete search history.

(56) References Cited

OTHER PUBLICATIONS

Yoon et al., Lee JM; Kim E et al. Quantitative liver function analysis: Volumetric T1 mapping with fast multisection B1 inhomogeneity correction in hepatocyte-specific contrast-enhanced liver MR imaging. Radiology 2016 [epub ahead of print].

Wood J., et al: "MRI R2 and R2* mapping accurately hepatic iron concentration in transfusion-dependent thalassemia and sickle cell disease patients", in BLOOD, www.bloodjournal.org, Aug. 2005, vol. 106, Nr.4); 2005.

Kukuk GM et al., Hittatiya K, Sprinkart AM et al. Comparison between modified Dixon MRI techniques, MR spectroscopic relaxometry, and different histologic quantification methods in the assessment of hepatic steatosis. Eur Radiol 2015; 25: 2869-2879.

Haimerl M et al., Schlabeck M, Verloh N. et al. Volume-assisted estimation of liver function based on Gd-EOB-DTPA-enhanced MR relaxometry. Eur Radiol 2016; 26:1125-1133.

Ghugre N. et al: "Mechanisms of Tissue-Iron Relaxivity: Nuclear Magnetic Resonance Studies of Human Liver Biopsy Specimens", in Magn. Reson Med. 2005, Nov; 54(5): pp. 1185-1193, doi:10.1002/mr.20697; 2005.

Kramer H. et al., Pickhardt PJ, Kliewer MA et al. Accuracy of liver fat quantification with advanced CT, MRI, and ultrasound techniques: Prospective comparison with Mr Spectroscopy. AJR 2017; 208:1-9.

"Perspectum Diagnostics LMS Abridged.pdf", Multiparametric MRI for the liver, from: Liver Mulitscan Discover, Stand 2016.

Banerjee, Rajarshi et. al.: "Multiparametric magnetic resonance for non-invasive diagnosis of liver disease", in: EASL Journal of Hepatology, vol. 60, pp. 69-77, 2014.

Verloh N et al., Utpatel K, Haimerl M et al. Liver fibrosis and Gd-EOB-DTPA-enhanced MRI: A histopathologic correlation. Sci Rep. Oct. 19, 2015;5.

Horng DE et al., Hernando D, Reeder SB. Quantification of liver fat in the presence of iron overload. J Magn Reson Imaging 2016 (epub ahead of print).

* cited by examiner

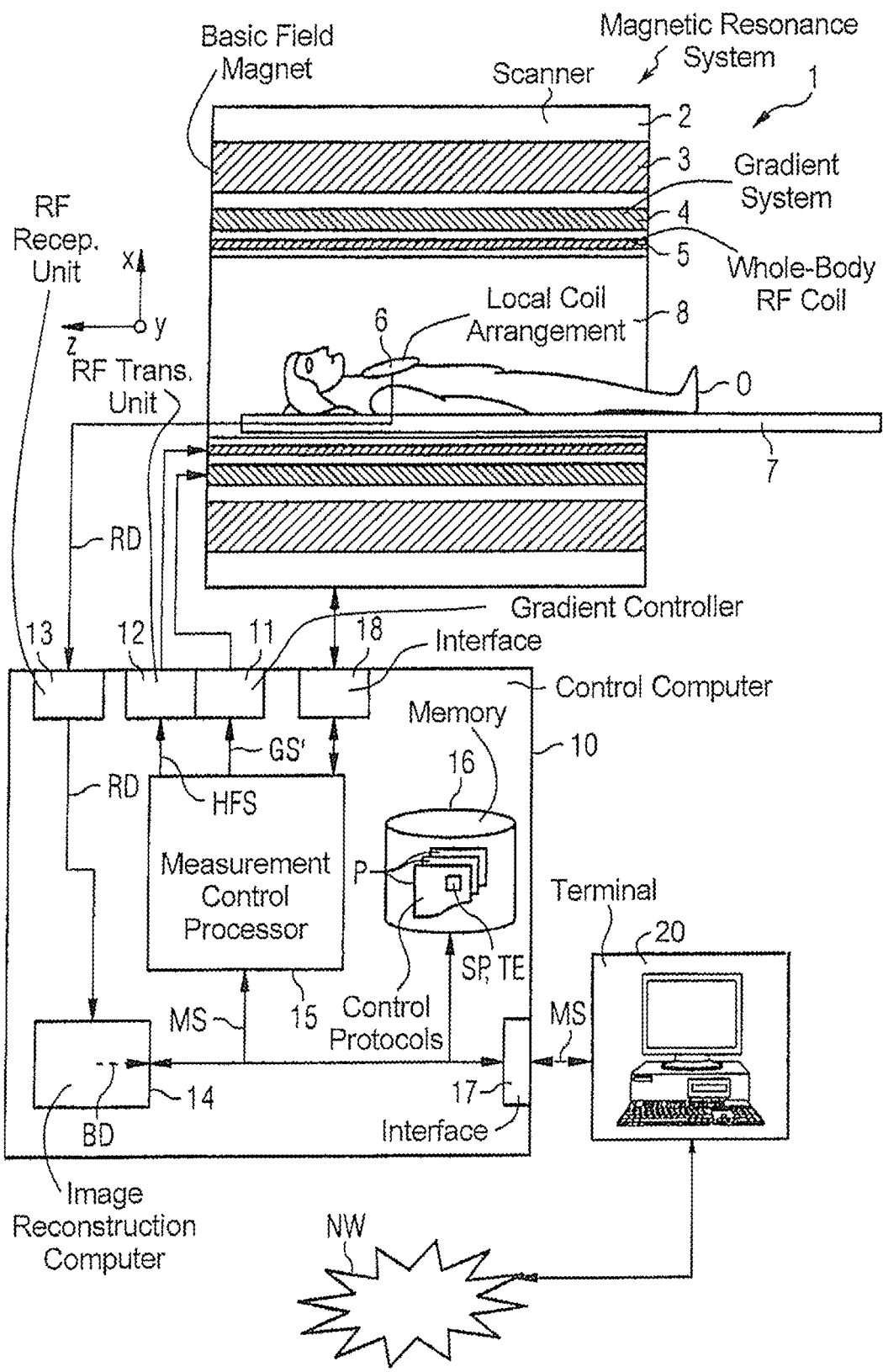

METHOD AND MAGNETIC RESONANCE APPARATUS FOR GENERATING A FAT FRACTION-CORRECTED T1 PARAMETER MAP

RELATED APPLICATION

Under 35 U.S.C. § 120, Applicant claims the benefit of the filing date of U.S. Provisional Application 62/482,929 filed Apr. 7, 2017.

BACKGROUND OF THE INVENTION

Field of the Invention

The present invention concerns the field of magnetic resonance imaging, and in particular to the generation of parameter maps, such as a T1 parameter map.

Description of the Prior Art

Magnetic resonance (MR) imaging, also called MR tomography, is a known imaging modality in widespread use in various fields, including medicine. In general terms, in order to generate an MR image of a subject, the subject is initially placed in a strong, constant and homogeneous basic magnetic field, which causes nuclei in the subject to be aligned in the direction of the basic magnetic field. Radio-frequency (RF) energy is then radiated into the subject, usually in the form of RF pulses. The frequency of the RF energy causes certain nuclei to be excited. Each hydrogen nucleus represents a magnetic dipole, and expectation values of the magnetic axes of the excited nuclear spins are caused by the RF energy to deviate from the field lines of the basic magnetic field by an amount known as a flip angle. As these excited nuclei relax and return to the equilibrium state, the transverse components of the excited spins induce a voltage in the receive coils that is measured. Furthermore the received magnetic resonance signals are spatially encoded by gradient magnetic fields, and are entered into a memory as raw data. The raw data can be transformed into image data by a mathematical procedure, which in the most conventional approaches corresponds to a Fourier transformation. The image data are provided to a display monitor, at which an image of the subject is then displayed. In the case of medical MR imaging, wherein the subject is a patient, different types of tissue in the patient exhibit different relaxation times, and thus can be differentiated as different contrasts in the MR image. Two basic tissue categories in human patients are tissue predominantly composed of fat and tissue predominantly composed of water. These different types of tissue are commonly referred to as fat compartments and water compartments in the body of a patient.

In general terms, however, each picture element (i.e., a pixel in the case of a 2D image or a picture element in the case of a 3D image) can contain signal contributions from two or more compartments, whose respective signals contribute to the total signal represented by the picture element, in an additive fashion. Each compartment is associated with a chemical species.

After excitation, the nuclei (nuclear spins) start to relax back towards the equilibrium, as noted above. More specifically, the expectation values of the transverse magnetization and of the longitudinal magnetization decay exponentially towards their equilibrium values, as determined by the Bloch equation. The equilibrium value of the transverse magnetization is zero. The relaxation times of those exponential evolutions that correspond to the inverse decay rates are hereby referred to as T1 for the longitudinal relaxation and T2 for the transverse relaxation.

The compartment associated with fat is known to show only small variations or dependencies on the surrounding tissue. Therefore, MR parameters for the fat compartment can be considered as known. In particular, the T1 value of fat is known to be small, and to vary only slightly.

Several clinically established MR data acquisition techniques are known in order to determine the fraction or ratio of water and fat compartments.

Measurements having the object of determining T1 values of a picture element can receive signals from multiple compartments. In the case of water and fat, the T1 values of water and fat may differ, and the T1 value of water is the quantity of interest.

For determining the T1 value of water, two scenarios are conceivable.

A first scenario is that the water/fat fraction is known from a separate measurement. In this scenario, the signal contribution of fat can be modeled, and only the T1 value of water is then determined, by fitting a model to the acquired data.

In another scenario, the techniques to determine the fat/water fraction, and T1, may be combined. United States Patent Application Publication No. 2015/0042334 uses a multi-echo Dixon technique with a variable flip angle for T1 mapping. More relevant, however, is inversion recovery for T1 mapping.

SUMMARY OF THE INVENTION

The basis of the invention is the insight that, with known acquisition parameters, relaxation times can be calculated for the water compartment if additionally, the fat fraction of the MR signal is provided. The fat fraction of the MR signal can be determined with commercially available MR data acquisition scanners. The T1 time of fat can be assumed as a constant, or as very small. The invention is further based on the insight that the relaxation times of fat are, in a first order representation, universally equal, and that fat does not mix in water. In a higher order evaluation, which can be neglected depending on the desired precision, effects such as susceptibility or transfer effects may have an influence. Because those effects act on water and fat compartments in the same way, they can still be considered. For a known fat content/fraction, the relative signal of fat thus can be modeled and considered in the determination of the relaxation times for the water compartment.

In accordance with the invention, the fat signal is considered as known when determining MR parameters, and its contribution is modeled when extracting the parameters of the water compartment. In an extreme case, the water and fat contributions can be modeled by Bloch equations, which contain couplings representing the aforementioned susceptibility and magnetization transfer effects. For established methods, analytical solutions and modelings are available.

Besides fat, other materials or spin species can be considered as known, such as silicon.

In the case of determination of T1 and knowledge of the fat fraction, the T1 of the water compartment can be determined. Since the T1 value of fat is typically much smaller than that of water, the dependence on the exact value of T1 for fat is generally weak.

The method can function with different types of mapping techniques, in particular inversion based techniques, such as Look-Locker, MOLLI, inversion spin echo, as well as steady state techniques such as with variable flip angles, variable repetition times (TR), as well as techniques with different contrasts, such as MESE.

Particularly, in the case of liver diagnosis, T1 mapping is correlated with extra cellular fluid volume, which can be used as a measure or indicator of the presence of or the risk of pathologies. The precision of such conclusions can be improved with a T1 parameter map corrected according to the fat fraction, in accordance with the invention.

Corrections of T1 values using a known fat fraction, wherein the correction is not based on detailed modeling, but is instead based on an empirically measured relation, are possible. This is particularly conceivable when the mapping technique is not changed, and the effect of fat on known relaxation times always acts in the same way, and thus can be calibrated.

The present invention, in addition to the aforementioned method, also encompasses a magnetic resonance apparatus designed to implement such a method. The invention also encompasses a non-transitory, computer-readable data storage medium encoded with programming instructions that, when the storage medium is loaded into a computer of a magnetic resonance apparatus, cause the computer to implement the method according to the invention, as described above.

DESCRIPTION OF THE DRAWING

The single FIGURE is a schematic illustration of magnetic resonance imaging apparatus constructed and operating in accordance with the present invention.

DESCRIPTION OF THE PREFERRED EMBODIMENTS

A magnetic resonance system 1 according to the invention is schematically shown in the FIGURE. It includes the actual magnetic resonance scanner 2 with an examination space or patient tunnel located therein. A bed 7 can be driven into this patient tunnel 8, such that a patient O or examination subject lying on the bed 7 can be supported at a defined position within the magnetic resonance scanner 2 relative to the magnet system and radio-frequency system arranged therein during an examination, or can be moved between different positions during a measurement.

Basic components of the magnetic resonance scanner 2 are a basic field magnet 3, a gradient system 4 with magnetic field gradient coils to generate magnetic field gradients in the x-, y- and z-directions, and a whole-body radio-frequency (RF) antenna 5. The magnetic field gradient coils can be controlled independently of one another in the x-, y- and z-directions so that gradients can be applied in arbitrary logical spatial directions (for example in the slice-selection direction, in the phase coding direction or in the readout direction) via a predetermined combination, wherein these directions normally depend on the selected slice orientation. The transmission (radiation) of RF signals can take place via the whole-body antenna 5. The MR signals are received with a local coil 6, which can be composed of one or more individual reception coils. The local coil 6 can also be used to radiate the RF signals. All of these components are known in principle to those skilled in the art and therefore are only schematically shown in FIG. 1.

The components of the magnetic resonance scanner 2 are controlled by a control computer, which can be formed by a number of individual computers (which may be spatially separated and connected among one another via suitable cables or the like). This control computer 10 is connected via a terminal interface 17 with a terminal 20 via which an operator can control the entire system 1. In the present case, this terminal 20 (as a computer) is equipped with keyboard, one or more monitors and additional input devices (for example mouse or the like) so that a graphical user interface is provided to the operator.

Among other things, the control computer 10 has a gradient controller 11 that can in turn have multiple sub-components. Via this gradient controller 11, the individual gradient coils are provided with control signals according to a gradient pulse sequence GS. These gradient pulses are radiated (activated) at precisely provided time positions and with a precisely predetermined time curve during a measurement.

The control computer 10 also has a radio-frequency transmission unit 12 in order to feed electrical signals respectively representing radio-frequency pulses into the whole-body radio-frequency coil 5 (or the local coil 6) according to a predetermined radio-frequency pulse sequence RFS of the pulse sequence MS. The radio-frequency pulse sequence RFS includes excitation and/or refocusing pulses. The reception of the magnetic resonance signals then occurs with the use of the reception coils of the local coil 6, and the raw data RF received in this manner are read out and processed by an RF reception unit 13. The magnetic resonance signals are passed in digital form as raw data RF to a reconstruction computer 14, which reconstructs the image data BD from the raw data using the reconstruction algorithm described above, and stores the image data BD in a memory 16 and/or passes the image data BD via the interface 17 to the terminal 20 so that the operator can view the image. The image data BD can also be stored at other locations via a network NW and/or be displayed and evaluated.

Control commands are transmitted via an interface 18 to other components of the magnetic resonance scanner 2 (such as the bed 7 or the basic field magnet 3, for example), and measurement values or other information are received.

The gradient controller 11, the RF transmission unit 12 and the RF reception unit 13 are controlled, in a coordinated manner, by a measurement control processor 15. Via corresponding commands, this ensures that the desired gradient pulse sequences GS and radio-frequency pulse sequences RFS are emitted. Moreover, for this purpose it must be ensured that the magnetic resonance signals are read out by the reception coils of the local coil array 6 by the RF reception unit 13 at the appropriate point in time and are processed further. The measurement control processor 15 likewise controls the interface 18.

In accordance with the invention, the T1 of fat and the fat fraction are used as known parameters in a model for determining T1 of another substance, such as water.

Several techniques are known to determine T1, which are based on applying a preparation pulse and then measuring the relaxation curve. Images are determined for a set of points sampled from the relaxation curve. The T1 value parameter maps are then determined by picture element-by-picture element fitting of the data points to a signal model.

Established versions for doing so are the conventional inversion recovery technique, and the Look-Locker technique.

In the conventional inversion recovery technique, the preparation is an inversion. Multiple inversion pulses are needed. For each inversion, only one data point along the relaxation curve is measured (detected). The corresponding inversion time (which is the time after the inversion pulse)

is varied. Otherwise the inversion takes place without intervention. This known procedure is very slow, but is usually considered the most accurate standard.

In the known Look-Locker technique, after inversion, multiple FLASH data acquisitions are continuously performed. The relaxation is not free (undisturbed), but the effect of the continuous FLASH acquisitions can be considered as the signal model. Multiple images are determined with different inversion times for a single inversion pulse. This makes the Look-Locker technique more efficient.

Another known technique is saturation recovery. In this technique, instead of an inversion pulse, a saturation pulse is used, which makes the saturation recovery technique more controlled in the subsequent MR measurement (data acquisition).

Another known technique is the MOLLI data acquisition procedure. This is similar to the conventional inversion recovery technique. Images at multiple inversion times are acquired using a fast acquisition technique, typically neglecting the effect of imaging acquisition on the relaxation curve In accordance with the invention, it is assumed that T1 and the fat fraction (FF) are known. The overall proton density (i.e., the sum of water and fat) is a part of the signal model for the T1 of the water compartment. The acquired data are fit to:

$$T_{1\,water}=\text{avgmin}_{T_{1water}}\Sigma(D-\rho FFf(T,T_{1fat})-\rho(1-FF)f(t,T_{1water}))^2$$

In the above, D represents the acquired data, and the summation is the sum over all acquired inversions. $\rho$ and $T_{1water}$ are the fit parameters.

In the context of a FLASH steady state model, the steady state signal of a compartment is given by $$S_{FLASH} = \rho\sin\alpha\frac{1-e^{-T_R/T_1}}{1-\cos\alpha e^{-T_R/T_1}}$$

wherein $\alpha$ is the flip angle, $T_R$ is the repetition time and $\rho$ is the proton density. There are established methods that determine T1 by doing at least two acquisitions, with different $T_R$ or $\alpha$. T1 is determined by fitting the signal model as to T1 and $\rho$. In accordance with the invention, it is assumed that the fat fraction is given, and fit to $$S_{FLASH} = \rho FF\frac{1-e^{-T_R/T_{1fat}}}{1-\cos\alpha e^{-T_R/T_{1fat}}} + \rho(1-FF)\frac{1-e^{-T_R/T_{1water}}}{1-\cos\alpha e^{-T_R/T_{1water}}}$$

wherein $\rho$ and $T_1$ again are the fit parameters.

In a further embodiment that can be characterized as joint fitting, the fat fraction is also determined by fitting to a dedicated signal model, typically multi-echo acquisitions. It may be advantageous to fit both models to both data sets simultaneously, since the value of the fat fraction affects both fits.

It is also possible to use multi-echo FLASH in T1 mapping, specifically in the context of the Look-Locker technique and the FLASH steady state technique. In that case, the fat fraction is part of the signal model, similar to joint fitting described above.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A method for generating a T1 parameter map comprising:
    operating a magnetic resonance (MR) data acquisition scanner in order to execute an MR data acquisition sequence in which MR signals emitted by selected nuclear spins in an examination subject are acquired with multiple contrasts depending on a longitudinal relaxation time T1, and to enter raw MR data, representing said MR signals, into a memory;
    from a computer, accessing said raw MR data from said memory and applying said raw MR data as a fit parameter in a model, for which T1 of fat is known, using a fat fraction of said MR signals as a known parameter in said model, in order to produce fat fraction-corrected T1 values from said raw MR data;
    in said computer, generating a T1 parameter map comprising said fat fraction-corrected T1 values; and
    visually presenting said T1 parameter map at a display screen in communication with said computer.

2. A method as claimed in claim 1 comprising using a model based on a Look-Locker technique to generate said T1 parameter map.

3. A method as claimed in claim 1 comprising using an inversion recovery model in order to generate said T1 parameter map.

4. A method as claimed in claim 1 comprising using a saturation recovery-based model in order to generate said T1 parameter map.

5. A method as claimed in claim 1 comprising using a modified Look-Locker inversion recovery (MOLLI)-based model in order to generate said T1 parameter map.

6. A method as claimed in claim 1 comprising operating said MR data acquisition scanner in order to execute a FLASH sequence as said MR data acquisition sequence.

7. A magnetic resonance (MR) apparatus comprising:
    an MR data acquisition scanner;
    a computer configured to operate said MR data acquisition scanner in order to execute an MR data acquisition sequence in which MR signals emitted by selected nuclear spins in an examination subject are measured with multiple contrasts depending on a longitudinal relaxation time T1, and to enter raw MR data, representing said MR signals, into a memory;
    said computer being configured to access said raw MR data from said memory and to apply said raw MR data as a fit parameter in a model, for which T1 of fat is known using a fat fraction of said MR signals as a known parameter in said model, in order to produce fat fraction-corrected T1 values from said raw MR data;
    said computer being configured to generate a T1 parameter map comprising said fat fraction-corrected T1 values; and
    visually presenting said T1 parameter map at a display screen in communication with said computer.

8. An MR apparatus as claimed in claim 7 wherein said computer is configured to use a model based on a Look-Locker technique to generate said T1 parameter map.

9. An MR apparatus as claimed in claim 7 wherein said computer is configured to use an inversion recovery model in order to generate said T1 parameter map.

10. An MR apparatus as claimed in claim 7 wherein said computer is configured to use a saturation recovery-based model in order to generate said T1 parameter map.

11. An MR apparatus as claimed in claim 7 wherein said computer is configured to use a modified Look-Locker inversion recovery (MOLLI)-based model in order to generate said T1 parameter map.

12. An MR apparatus as claimed in claim 7 wherein said computer is configured to operate said MR data acquisition scanner in order to execute a FLASH sequence as said MR data acquisition sequence.

13. A non-transitory, computer-readable data storage medium encoded with programming instructions, said storage medium being loaded into a computer of a magnetic resonance (MR) apparatus that comprises an MR data acquisition scanner, said programming instructions causing said computer to:

operate said MR data acquisition scanner in order to execute an MR data acquisition sequence in which MR signals emitted by selected nuclear spins in an examination subject are measured with multiple contrasts depending on a longitudinal relaxation time T1, and to enter raw MR data, representing said MR signals, into a memory;

access said raw MR data from said memory and apply said raw MR data at a fit parameter in a model, using a fat fraction of said MR signals as a known parameter, in order to produce fat fraction-corrected T1 values from said raw MR data;

generate a T1 parameter map comprising said fat fraction-corrected T1 values; and visually present said T1 parameter map at a display screen in communication with said computer.

14. A method for generating a T1 parameter map comprising:

operating a magnetic resonance (MR) data acquisition scanner in order to execute an MR data acquisition sequence in which MR signals emitted by selected nuclear spins in an examination subject are measured with multiple contrasts depending on a longitudinal relaxation time T1, and to enter raw MR data, representing said MR signals, into a memory;

from a computer, accessing said raw MR data from said memory and applying said raw MR data as a fit parameter in a model, for which T1 of fat is known, with a fat fraction of said MR signals being produced as a fitted parameter in said model, in order to produce fat fraction-corrected T1 values from said raw MR data;

in said computer, generating a T1 parameter map comprising said fat fraction-corrected T1 values; and visually presenting said T1 parameter map at a display screen in communication with said computer.

* * * * *